United States Patent [19]

Strassmann

[11] Patent Number: 4,838,859

[45] Date of Patent: Jun. 13, 1989

[54] STEERABLE CATHETER

[75] Inventor: Steve Strassmann, 796 Main St., Cambridge, Mass. 02139

[73] Assignee: Steve Strassmann, Cambridge, Mass.

[21] Appl. No.: 52,263

[22] Filed: May 19, 1987

[51] Int. Cl.$^4$ .......................................... A61M 37/00
[52] U.S. Cl. ..................................................... 604/95
[58] Field of Search ............................................ 604/95

[56] References Cited

U.S. PATENT DOCUMENTS

| | | | |
|---|---|---|---|
| 3,552,384 | 1/1971 | Plerle | 604/95 X |
| 3,773,034 | 11/1973 | Burns | 128/348 X |
| 3,890,977 | 3/1974 | Wilson | 128/418 |
| 4,066,070 | 1/1978 | Utsugi | 604/95 X |
| 4,176,662 | 12/1979 | Frazer | 604/95 X |
| 4,207,872 | 6/1980 | Meiri et al. | 604/95 X |
| 4,207,873 | 6/1980 | Kruy | 128/6 |
| 4,286,585 | 9/1981 | Ogawa | 128/6 |
| 4,461,282 | 6/1984 | Ouchi | 128/4 |
| 4,483,326 | 11/1984 | Yamaka | 128/4 |
| 4,503,842 | 3/1985 | Takayama | 128/4 |
| 4,543,090 | 10/1985 | McCoy | 604/95 |
| 4,545,390 | 10/1985 | O'Leary | 604/95 X |
| 4,601,705 | 7/1986 | McCoy | 604/95 |
| 4,619,263 | 10/1986 | Frisbie | 604/96 X |

Primary Examiner—Allen M. Ostrager

[57] ABSTRACT

Steerable catheters are achieved using a filament which changes its configuration in response to a changed environmental condition (e.g. temperature) and a controller to change that environmental condition as desired. Alternatively, inflatable members can be used to steer the catheter by deflecting its tip. Catheter propulsion is achieved using an inflatable member which creates a wave-action as it is inflated. Finally, multiple tendons, connected in mirror image positions at the catheter handle and tip, respectively, reflect manipulation of the handle in the tip, to facilitate steering the tip.

2 Claims, 4 Drawing Sheets

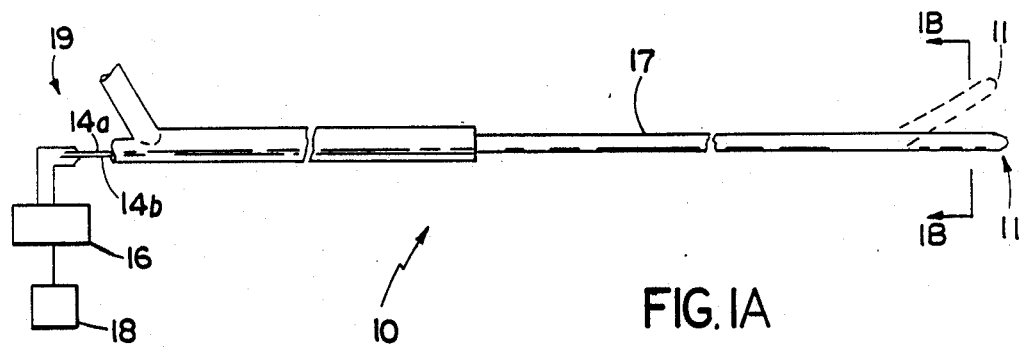
FIG. IA
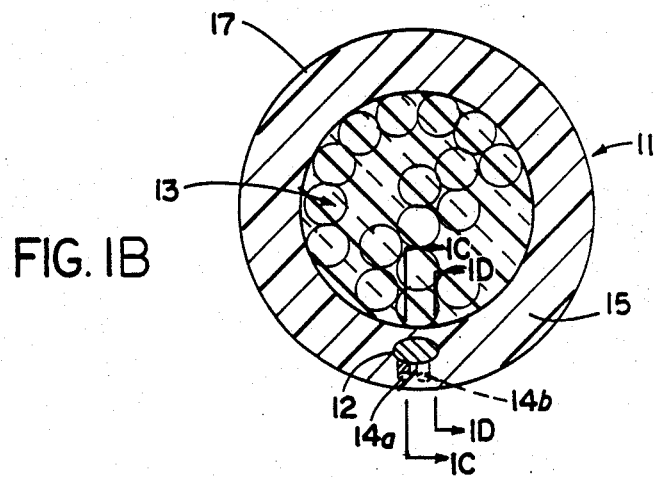
FIG. IB
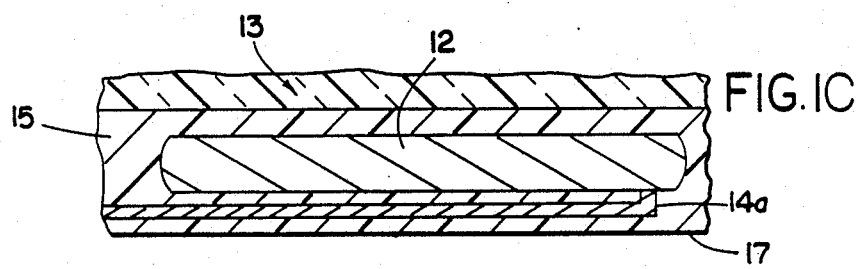
FIG. IC
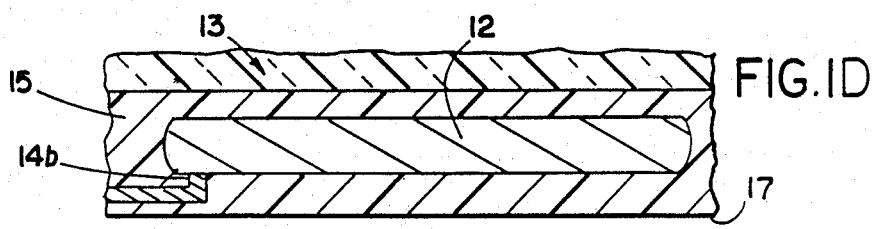
FIG. ID

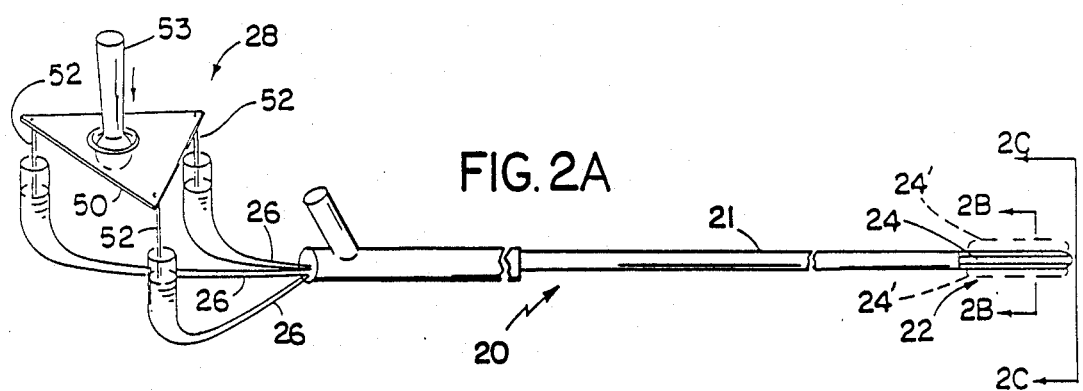
FIG. 2A
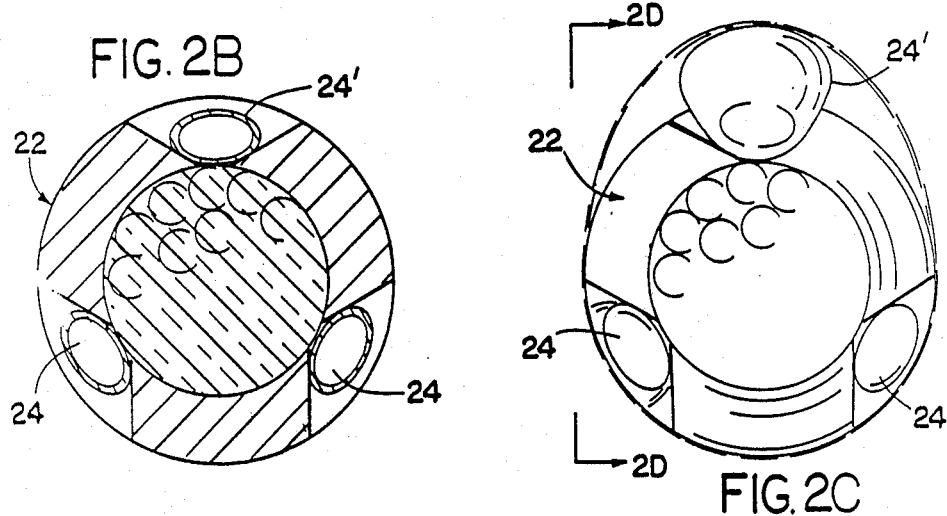
FIG. 2B
FIG. 2C
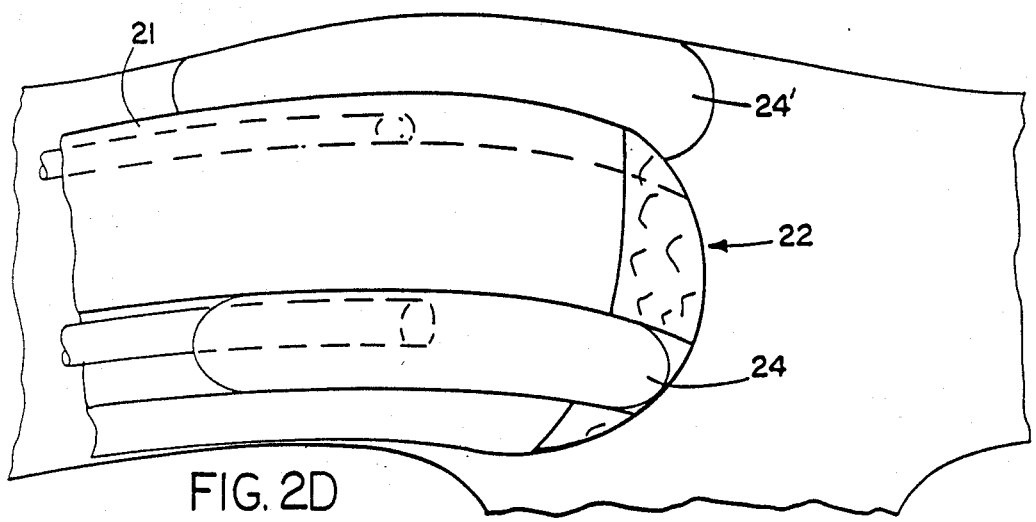
FIG. 2D

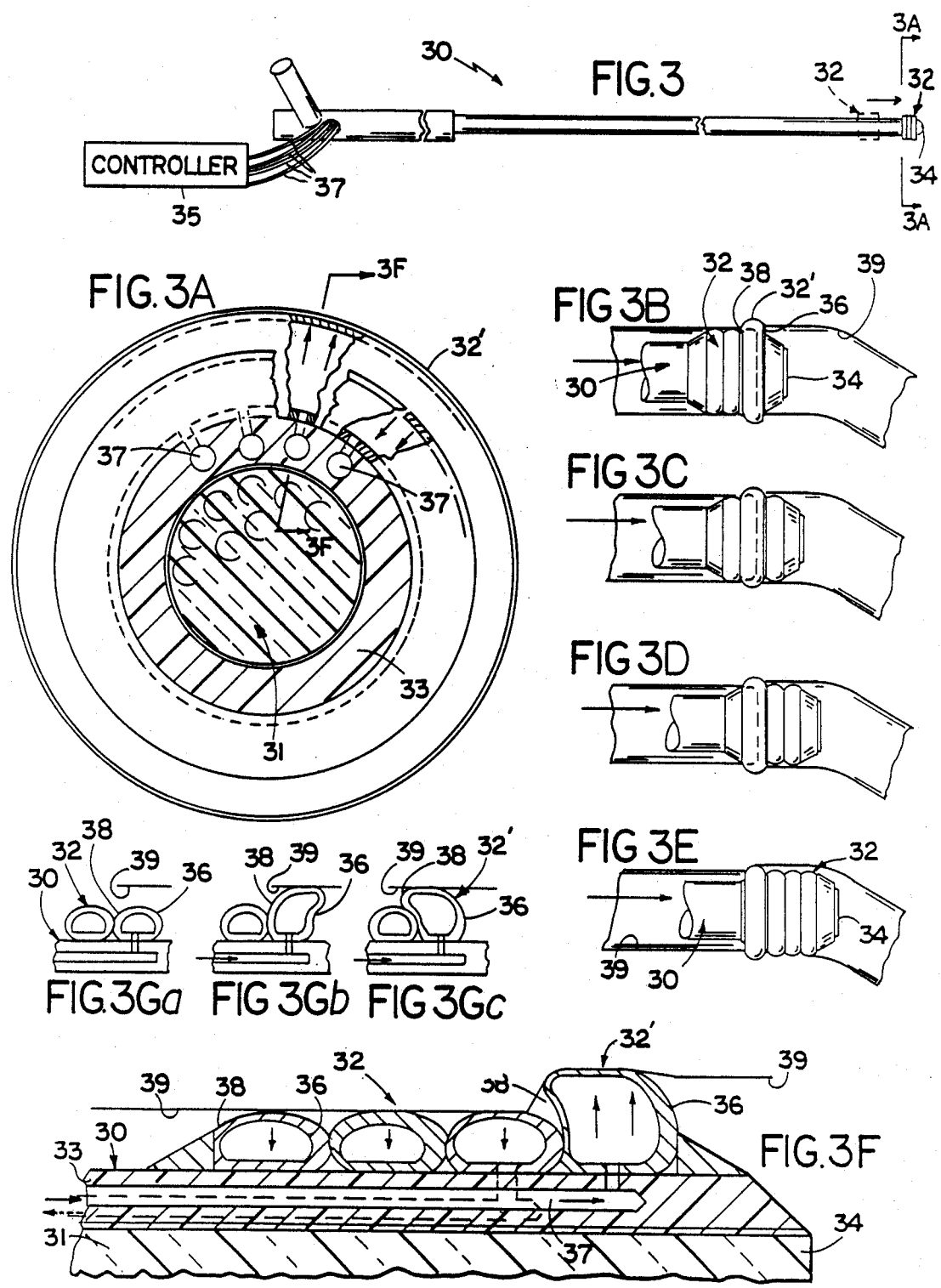

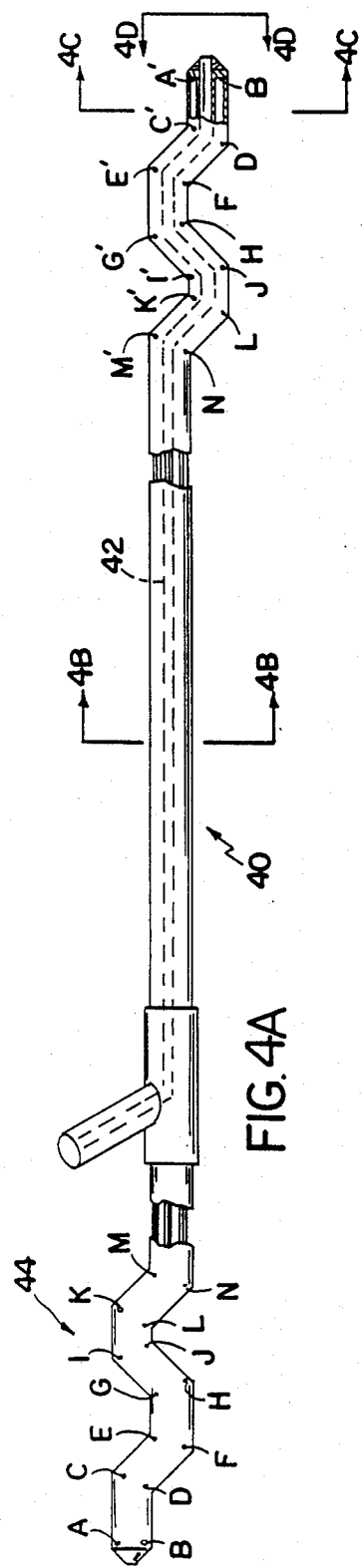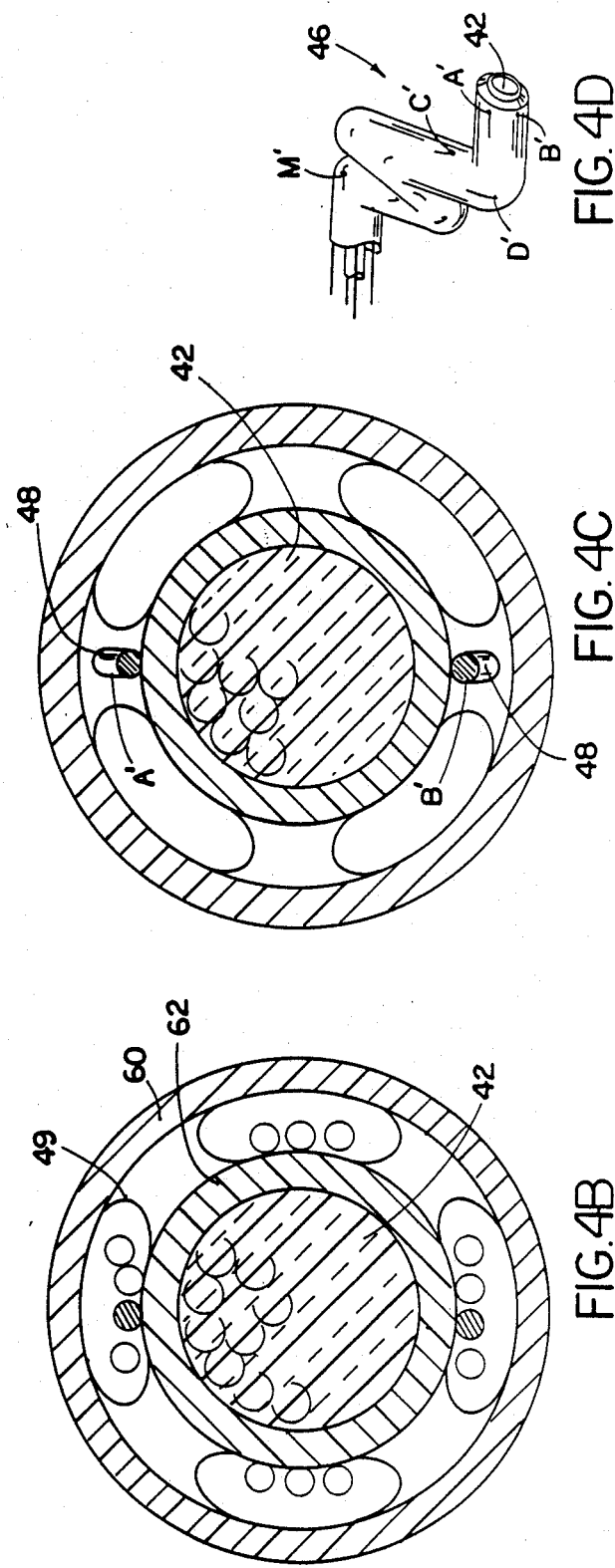

4,838,859

STEERABLE CATHETER

BACKGROUND OF THE INVENTION

This invention relates to steerable catheters, for example, medical catheters used in angiography, endoscopy or angioplasty.

In general, the term catheter as used in this application includes a wide variety of devices for accessing a remote location, particularly medical devices for inspecting, assaying or operating on interior bodily tissue. For example, catheters may be used to sample tissue or fluid, or to administer drugs, radiation, heat, laser light, or an electric stimulus to a selected remote location. They may be used to inspect a remote location using fibre optics. Catheters also may be used for remote physiological measurements—e.g. heat, electrical impulses (EKG), pH, or chemical assays.

A wide variety of medical catheters are known; for example, catheters such as the cather disclosed in O'Leary U.S. Pat. No. 4,545,390 are used to dilate coronary arteries or to perform coronary angioplasty. Another common type of catheter is the endoscope.

Catheters also may be used industrially to access remote locations in equipment such as a heat exchanger having tortious tubing or spaces.

One serious difficulty with catheters is accessing the correct branch where a pathway (e.g. an artery) branches. For example, a catheter may be introduced into a coronary artery via another, more accessible artery, such as a femoral artery. The catheter must be advanced along the arterial system through numerous branches until it is properly located in a coronary artery. The physician inserting the catheter must advance it carefully, without damaging tissue, and without allowing it to venture into the wrong path. Access to the desired branches may require sharp bends first in one and then in another direction. It is highly desirable to be able to steer the catheter, yet the nature of the environment of use makes visualization and steering difficult.

Often guidewires may be used to advance the catheter, and catheters having steerable guidewires are known. For example, O'Leary U.S. Pat. No. 4,545,390 discloses a coronary dilatation catheter with a steerable guidewire. The guidewire has torsional rigidity to transmit a twist from the proximal end to the distal end. The distal end can be bent manually by the surgeon and will retain its bent configuration. The catheter is steered by rotation of the guidewire to direct the curved distal end selectively into the desired arterial branches.

Other steerable catheters are disclosed in Frisbie U.S. Pat. No. 4,619,263, Plerle U.S. Pat. No. 3,552,384 and Kaldenbach, European Heart Journal (1984) 5:1000-1009.

Takayama U.S. Pat. No. 4,503,842 discloses apparatus to control the deflection of the tip of an endoscope, by means of angulation wires secured to the distal end of the endoscope. The angulation wires are looped around wire drums which in turn are driven by motors. Other similar endoscope tip angulation control mechanisms are shown in Yamaka U.S. Pat. No. 4,483,326; Ouchi U.S. Pat. No. 4,461,282, Ogawa, U.S. Pat. No. 4,286,585 and Kruy U.S. Pat. No. 4,207,873.

SUMMARY OF THE INVENTION

The invention features improvements to catheters comprising a conduit extending from a control region to a functional tip region.

In a first aspect, the improvement comprises: (a) at least one filament connected to the functional tip region, comprising a material which, in response to a changed environmental condition, reversibly alters its degree of curvature; and (b) means to change the environmental condition at the tip, responsive to a controller positioned toward the control region. Activating the controller changes the environmental condition and changes the filament curvature. In that way, the catheter operator can cause the filament to curve and can steer the catheter in the direction of the curve.

Preferred embodiments of the first aspect have the following features. The environmental change is a change in temperature, and the means to change the environmental condition comprises a resistance element with means to apply a voltage across the resistance element. The filament comprises a metal filament (e.g. a nitinol alloy); alternatively it is a bi-metal strip, comprising at least two attached metal strips having different coefficients of thermal expansion) that bends in response to temperature change.

In a second aspect, the improvement comprises: (a) at least one inflatable member positioned adjacent the tip region, the member, when inflated, being radially displaced in a known direction from the tip; and (b) means inflate the member responsive to a controller positioned toward the control region. Activating the controller to inflate the member steers the catheter tip in the direction opposite from the member.

In preferred embodiments of the second aspect, the inflatable member is a bladder, most preferably a plurality of inflatable bladders, each of the bladders being positioned adjacent and radially displaced from the tip in a different known direction. The catheter includes means to inflate each of the bladders individually, responsive to control means positioned toward the upstream end. The means to inflate the bladders can comprise a plurality of hydraulic pressurizing means, each of the pressurizing means being connected to a different bladder; the control can comprise a lever connected to a swivel platform, the platform being connected to each of the hydraulic pressurizing means. Lever motion swivels the platform to activate a desired hydraulic cylinder and thereby activates a desired bladder (or set of bladders), steering the catheter in a predetermined direction. As an alternative to discrete bladders, the catheter can include a flexible external skin having a more elastic region adapted to expand responsive to a lower fluid pressure than other regions of the skin.

In a third aspect, the improvement comprises an inflatable locomotion member, positioned at the catheter tip, which has an expandible skin that establishes a paristaltic wave longitudinally along the skin, in the tip-to-control direction. The wave advances the tip axially in the tip-to-control direction.

One preferred locomotion member is an inflatable member (e.g. a bladder) that changes its position with increasing internal pressure. For example, the locomotion member can be a ladder that: (a) is annularly shaped and is positioned around the catheter axis; (b) has a thin wall portion positioned on the side of the bladder toward the control region; and (c) has a thick-wall portion positioned on the side of the bladder toward the functional catheter tip region. As the bladder expands in response to increasing pressure, it first moves tipward as the thin-wall portion expands until it engages its external environment (e.g. a vessel wall). Then the bladder moves away from the tip as the thick wall portion expands, advancing the catheter.

In preferred embodiments of the third aspect, (a) the bladder is annularly shaped and is positioned around the catheter axis; b) the thin-wall portion is positioned on the side of the bladder toward the control region; and (c) the thick wall portion is positioned on the side of the bladder toward the functional catheter tip region, whereby the bladder expands in a wave from the tip to the control region, causing the catheter to advance axially in the tip direction. Also, the catheter may comprise a plurality of the bladders, arranged along the catheter axis, and means to activate the bladders sequentially.

In a fourth aspect, the improvement comprises a plurality of tendons, each tendon being attached to a different point adjacent the catheter tip, which is flexible, and to corresponding points positioned in a mirror image pattern adjacent the control end. Each tendon is generally of a length corresponding to the straight-line distance between its points of attachment, so that movement of the control end induces corresponding movement in the functional tip.

The invention provides suitable control means for steering the catheter at will in a demanding environment.

Other features and advantages of the catheter will be apparent from the following description of the preferred embodiments and from the claims.

DESCRIPTION OF THE PREFERRED EMBODIMENTS

I first briefly describe the drawings of preferred embodiments of the invention.

FIG. 1A is a diagrammatic side view of a catheter with the memory filament steering feature.

FIG. 1B is a section along 1B—1B of FIG. 1A.

FIG. 1C is a section along 1C—1C of FIG. 1B.

FIG. 1D is a section along 1D—1D of FIG. 1B.

FIG. 2A is a diagrammatic side view of a catheter with the bladder steering feature.

FIG. 2B is an end view of the catheter of FIG. A, taken at 2B—2B.

FIG. 2C is an end view of the catheter of 2A with bladder 24' inflated.

FIG. 2D is a side view taken along 2D—2D of FIG. 2C.

FIG. 3 is a diagrammatic side view of a catheter with the bladder propulsion feature.

FIG. 3A is a section taken at 3A—3A of FIG. 3.

FIG. 3B is an enlarged view of the tip of the bladder of FIG. 3.

FIGS. 3C-3E are time sequence view of the tip shown in FIG. 3B.

FIG. 3F is a section taken at 3F—3F of FIG. 3A.

FIG. 3G is a time sequence view of inflation of bladder 32'.

FIG. 4A is a diagrammatic side view of a catheter with the multiple tendon steering feature.

FIGS. 4B and 4C are sections taken at 4B—4B and at 4C—4C, respectively, in FIG. 4A.

FIG. 4D is a view taken at 4D of FIG. 4A.

The following description of each of those embodiments are illustrative of the invention.

1. Memory Filament

FIGS. 1A-1D are highly schematic representations of a fiber optic catheter 10, having a central optical fiber 13 surrounded by a sheath 17. In general catheter 10 is designed for insertion into the human body to visualize internal tissue at tip 11. The control end 19 includes appropriate apparatus for illuminating and viewing tissue at tip 11. These features are well known, and need not be repeated here.

A memory filament 12 is attached to the side of the tip of optical fiber 13 to aid in guiding and steering the catheter tip while it is inserted, or while it is being used for visualizing tissue. Specifically, a layer of silicon 15 is potted around fiber 13. Filament 12 is potted in silicon 15, with contact windows at opposite ends of filament 12. Conductors 14a and 14b are printed over the silicon so that one of the conductor 14a makes electrical contact with filament 12 at one end, and the other conductor 14b makes contact at the opposite end.

Conductors 14a and 14b extend along fiber 13 to voltage source 16 controlled by controller 18 and control end 19. FIGS. 1B and 1C show the catheter components in section. A preferred material for the memory filament 12 is nitinol, a titanium nickel alloy (available from Toki (US), Inc. Irvine Calif.) which has a "memory", responsive to heat.

The nitinol filament may be about 2-10 mils in diameter, and 1-2 inches long (e.g. Toki BH 420 is suitable). The filament may be manufactured to specification by Toki to have a transition temperature (the temperature at which curvature changes) of about 100°-105° F. Appropriate current and voltage are 10 mA and 3V, respectively, although these values will depend on the specific characteristics of the filament used. A suitable voltage source 16 is the Toki BH-525.

The nitinol filament is manufactured in a memory position (e.g. bent) and it is bent at room temperature to a straight position. So long as the filament is maintained below its transition temperature, it will retain its configuration. Heating the filament to cool below the transition causes it to bend. The response time for bending is extraordinarily rapid (1/1000 sec.). There is a very slight (5° C.) hysteresis, meaning that the transition than in the cooling cycle. A pulsing current may be used to maintain a desired temperature without overheating and without excessive cooling.

The catheter is introduced by known techniques and visualized by known techniques as it is advanced through the arterial systems. When a branch point is reached, the controller 18 is activated to send a small current through guide wire 12, causing it to heat by resistance heating. As the wire heats, it regains its original configuration during fabrication, as shown in the broken line in FIG. 1. In this way, the operator can guide or steer the catheter through the desired branch.

A number of memory filaments can be spaced evenly around the optical fiber by activating one or more filaments simultaneously, a nearly continuous range of tip orientations is possible. For example three filaments spaced 120° apart or four filaments 90° apart are sufficient to enable tip movement in any direction, providing extremely subtle control, without the torque required to orient a permanently bent guide wire.

2. Steering Bladders

FIGS. 2A-D disclose a second steerable catheter, which is a fiber optic catheter similar to the one in FIG. 1, except for the steering mechanism.

In FIG. 2A, catheter 20 has a tip 22 which has several (e.g. three) inflatable bladders 24 in the outer sheath 21, positioned circumferentially around tip 22. Each bladder 24 is attached to a hydraulic fluid line 26, and fluid lines 26 extend from the tip to control end of catheter 20 where they terminate at a controller 28. Controller 28 includes a swivel platform 50 attached to piston rods 52, each of which drives a separate fluid line 26. A joystick 53 controls the swivel of platform 50 and therefore the amount of hydraulic pressure applied to each bladder. Pivoting platform 50 increases pressure in specific bladder(s), while minimizing pressure in bladder(s) on the opposite side, deflecting the catheter tip and therefore steering it. Deflection in directions intermediate to a bladder are achieved by partial inflation of two adjacent bladders.

The bladders preferably are a polymeric material which expands to a predetermined size, without risk of further expansion which could damage a blood vessel, and without risk of explosion, which could release debris and suddenly increase pressure in the vessel. Polyethylene terephalate balloons (PET), as disclosed in Levy U.S. Pat. No. 4,490,421, hereby incorporated by references, are suitable. The hydraulic fluid is preferably a saline solution or other non-toxic liquid. In general, the inflation system shown in U.S. Pat. No. 4,195,637, also incorporated by reference, is suitable.

As shown in FIGS. 2C-2D, as lever 53 is moved in the direction of the arrow, one of the bladders (labeled 24') is inflated, bending tip 22 in the direction shown in FIG. 2D.

As an alternative to discrete bladders, a sheath having pre designed weak spots and internal hydraulic compartments for each weak spot may be used.

3. Bladder Propulsion

FIGS. 3-3F depict a third embodiment in which several (e.g. four) annular bladders 32 of variable wall thickness surround a catheter 30 near tip 34. Specifically, each bladder 32 has a thick-wall region 36 facing toward tip 34 and a thinner-walled region 38 facing in the opposite direction.

As shown in FIG. 3G, as a given bladder is inflated, the thin-wall region 38 will begin to inflate first and the bladder moves forward. With additional pressure, the bladder reaches the vessel wall, and thick-wall region 36 will begin to inflate at a greater rate, causing the bladder to move from front-to-back, as shown in FIGS. 3B-3E. Contact between the wave and the vessel 39 surrounding the catheter (e.g. a vessel wall) propels the catheter forward.

As shown in FIGS. 3A and 3F, each bladder 32 is connected to a separate hydraulic line 37, which is potted in a suitable (e.g. epoxy) sleeve 33 surrounding the central optical fiber 31. Lines 37 extend along the catheter to the controller 35 which can be similar to controller 28 of FIG. 2A or other known hydraulic control means. In FIGS. 3A and 3F, bladder 32' is expanded.

As discussed above PET or latex bladders are suitable. The desired wall thickness characteristic can be achieved by casting bladders 32 according to known techniques.

4. Multiple Tendons

FIGS. 4A-4D show an additional embodiment of a steerable catheter 40. Catheter 40 includes a core fiber optic conduit 42 extending from a control region 44 to a functional tip 46.

A series (e.g. 5-20) of tendons 48 are attached to the tip, each tendon being attached at one end to a different point (A'-J') axially along the tip and radially around the circumference of the tip. Each tendon is attached at its opposite end to point (A-J) in the control or handle region 60 of the catheter. Points A-J are positioned at mirror image locations to points A'-J', respectively. That is, the points are symmetrically placed about a central plane perpendicular to the catheter axis.

Since the tendons are designed to have a length approximately equal to the respective straight-line distance between points of attachment (e.g. between A and A'), manipulation of the handle region 60 is reflected by movement in the functional tip region.

The tendons can be suitable biocompatible metal filaments (e.g. stainless steel) attached by appropriate known techniques to the catheter.

As shown in greater detail in FIGS. 4B and 4C the tendons 48 are contained within a conduit 49 as they extend along the catheter to allow relatively unencumbered movement. Conduits 49 are formed by tubing potted between flexible (e.g. latex) layers 60 and 62 along the length of the catheter. At tip 46, the tendons 48 are connected to layer 62 as exemplified by points A' and B' in FIG. 4C.

Other embodiments are within the following claims.

I claim:

1. In a catheter comprising a conduit extending from a control end to a functional tip, an improvement comprising:
   an inflatable, annularly shaped bladder positioned around the catheter axis at the catheter tip,
   said bladder having a thin-walled portion positioned on the side of said bladder nearer the control end of the catheter, and a thick-walled portion positioned on the side of said bladder nearer the catheter tip; and
   means to inflate said bladder in response to a controller positioned at the control end of said catheter,
   whereby, as said bladder inflates, the thin-walled portion expands first until it engages its external environment, and then the thick-walled portion of said bladder expands and the thin-walled portion contracts, thereby creating a paristaltic wave along said bladder and advancing said catheter axially in the tip direction.

2. The catheter of claim 1 wherein said Catheter comprises a plurality of said bladders, arranged along the catheter axis, and means to activate the bladders sequentially.

* * * * *